United States Patent [19]
Popowski et al.

[11] Patent Number: 6,074,338
[45] Date of Patent: *Jun. 13, 2000

[54] MEDICAL APPLIANCES FOR THE TREATMENT OF BLOOD VESSELS BY MEANS OF IONIZING RADIATION

[75] Inventors: Youri Popowski; Vitali Verin, both of Genève, Switzerland

[73] Assignee: Schneider (Europe) A.G., Bulach, Switzerland

[*] Notice: This patent issued on a continued prosecution application filed under 37 CFR 1.53(d), and is subject to the twenty year patent term provisions of 35 U.S.C. 154(a)(2).

[21] Appl. No.: 08/276,219

[22] Filed: Jun. 28, 1994

[30] Foreign Application Priority Data

Jul. 1, 1993 [EP] European Pat. Off. ............. 93110531

[51] Int. Cl.$^7$ ...................................................... A61N 5/00
[52] U.S. Cl. ................................................................ 600/3
[58] Field of Search .................................... 600/1–3, 6, 7

[56] References Cited

U.S. PATENT DOCUMENTS

| | | |
|---|---|---|
| 1,442,051 | 1/1923 | Cummings . |
| 2,546,761 | 3/1951 | Loftus . |
| 2,862,108 | 11/1958 | Meilink . |
| 2,955,208 | 10/1960 | Stevens . |
| 3,060,924 | 10/1962 | Rush . |
| 3,147,383 | 9/1964 | Prest . |
| 3,324,847 | 6/1967 | Zoumboulis . |
| 3,505,991 | 4/1970 | Hellerstein et al. . |
| 3,643,096 | 2/1972 | Jeffries, Jr. et al. . |
| 3,669,093 | 6/1972 | Sauerwein et al. . |

(List continued on next page.)

FOREIGN PATENT DOCUMENTS

| | | |
|---|---|---|
| 2166915 | 8/1996 | Canada . |
| 0152124 A3 | 8/1985 | European Pat. Off. . |
| 0158630 A2 | 10/1985 | European Pat. Off. . |
| 0158630 A3 | 10/1985 | European Pat. Off. . |
| 0308630 A1 | 3/1989 | European Pat. Off. . |
| 0433011 A1 | 6/1991 | European Pat. Off. . |
| 0466681 A1 | 1/1992 | European Pat. Off. . |
| 0474994 A1 | 3/1992 | European Pat. Off. . |
| 0 514 913 A2 | 11/1992 | European Pat. Off. . |
| 0621015 A1 | 10/1994 | European Pat. Off. . |
| 0633041 A1 | 1/1995 | European Pat. Off. . |
| 0668088 A1 | 8/1995 | European Pat. Off. . |
| 0 688 580 A1 | 12/1995 | European Pat. Off. . |
| 0686342 A1 | 12/1995 | European Pat. Off. . |
| 0 696 906 B1 | 2/1996 | European Pat. Off. . |

(List continued on next page.)

OTHER PUBLICATIONS

Shirish K. Jani, Ph.D., "Debate: the Preferred Isotope Source—Beta Versus Gamma?", *Advances in Cardiovascular Radiation Therapy Syllabus*, Washington, D.C., Feb. 20–21, 1999, pp. 64–65.

Shirish K. Jani, Ph.D., "Beta vs. Gamma Sources", *Advances in Cardiovascular Radiation Therapy II*, Washington, D.C., Mar. 8–10, 1998, p. 195.

Peter R. Almond, Ph.D.., "Beta versus Gamma", *Advances in Cardiovascular Radiation Therapy II*, Washington, D.C., Mar. 8–10, 1998, p. 196.

Ron Waksman, M.D., "The Hottest Depate in Town: Gamma vs. Beta", *First Annual Symposium on Radiotherapy to Prevent Restenosis*, La Jolla, California, Jan. 10–11, 1997, pp. 49–50,Tjho–.

Heslinga et al., "Results of ruthenium irradiation of uveal melanona", *Radiothereapy Oncology*, vol. 29, pp 33–38, 1993.

(List continued on next page.)

*Primary Examiner*—Samuel Gilbert
*Attorney, Agent, or Firm*—Crompton, Seager & Tufte, LLC.

[57] ABSTRACT

A catheter with a balloon mounted coaxially thereon, and a radiation emitting source disposed and essentially centered in the catheter distal portion.

45 Claims, 3 Drawing Sheets

U.S. PATENT DOCUMENTS

| | | | |
|---|---|---|---|
| 3,674,006 | 7/1972 | Holmer | 600/3 |
| 3,750,653 | 8/1973 | Simon . | |
| 3,811,426 | 5/1974 | Culver et al. . | |
| 3,861,380 | 1/1975 | Chassagne et al. . | |
| 3,866,050 | 2/1975 | Whitfield . | |
| 3,927,325 | 12/1975 | Hungate et al. | 250/435 |
| 3,970,073 | 7/1976 | Greene . | |
| 4,096,862 | 6/1978 | DeLuca . | |
| 4,220,864 | 9/1980 | Sauerwein et al. . | |
| 4,225,790 | 9/1980 | Parsons, Jr. et al. . | |
| 4,244,357 | 1/1981 | Morrison . | |
| 4,281,252 | 7/1981 | Parsons, Jr. et al. . | |
| 4,314,157 | 2/1982 | Gaines . | |
| 4,364,376 | 12/1982 | Bigham . | |
| 4,402,308 | 9/1983 | Scott . | |
| 4,578,061 | 3/1986 | Lemelson | 604/164 |
| 4,584,991 | 4/1986 | Tokita et al. . | |
| 4,588,395 | 5/1986 | Lemelson | 604/59 |
| 4,610,662 | 9/1986 | Weikl et al. | 604/53 |
| 4,631,415 | 12/1986 | Sauerwein et al. . | |
| 4,697,575 | 10/1987 | Horowitz . | |
| 4,702,228 | 10/1987 | Russell, Jr. et al. . | |
| 4,706,652 | 11/1987 | Horowitz . | |
| 4,763,642 | 8/1988 | Horowitz . | |
| 4,763,671 | 8/1988 | Goffinet . | |
| 4,770,653 | 9/1988 | Shturman | 604/21 |
| 4,782,834 | 11/1988 | Maguire et al. . | |
| 4,784,116 | 11/1988 | Russell, Jr. et al. . | |
| 4,815,449 | 3/1989 | Horowitz | 600/7 |
| 4,819,618 | 4/1989 | Liprie | 600/7 |
| 4,842,590 | 6/1989 | Tanabe et al. | 604/282 |
| 4,851,694 | 7/1989 | Rague et al. . | |
| 4,861,520 | 8/1989 | van't Hooft et al. | 252/644 |
| 4,881,937 | 11/1989 | van't Hooft et al. . | |
| 4,891,165 | 1/1990 | Suthanthiran | 252/633 |
| 4,897,076 | 1/1990 | Puthawala et al. . | |
| 4,936,823 | 6/1990 | Colvin et al. . | |
| 4,940,452 | 7/1990 | Rohe et al. | 600/7 |
| 4,960,411 | 10/1990 | Buchbinder | 604/95 |
| 4,963,128 | 10/1990 | Daniel et al. . | |
| 4,969,863 | 11/1990 | van't Hooft et al. . | |
| 4,976,266 | 12/1990 | Huffman et al. . | |
| 4,976,680 | 12/1990 | Hayman et al. . | |
| 4,976,690 | 12/1990 | Solar et al. . | |
| 4,983,167 | 1/1991 | Sahota | 606/194 |
| 4,994,013 | 2/1991 | Suthanthiran et al. | 600/8 |
| 5,012,357 | 4/1991 | Schoeppel et al. | 600/7 |
| 5,030,194 | 7/1991 | Van't Hooft . | |
| 5,032,113 | 7/1991 | Burns . | |
| 5,059,166 | 10/1991 | Fischell et al. | 600/3 |
| 5,084,001 | 1/1992 | Van't Hooft et al. . | |
| 5,084,002 | 1/1992 | Liprie | 600/7 |
| 5,092,834 | 3/1992 | Bradshaw et al. | 600/7 |
| 5,103,395 | 4/1992 | Spako et al. . | |
| 5,106,360 | 4/1992 | Ishiwara et al. | 600/2 |
| 5,111,829 | 5/1992 | Alvarez de Toledo . | |
| 5,120,973 | 6/1992 | Rohe et al. | 250/497 |
| 5,139,473 | 8/1992 | Bradshaw et al. | 600/3 |
| 5,141,487 | 8/1992 | Liprie . | |
| 5,147,282 | 9/1992 | Kan | 600/1 |
| 5,163,896 | 11/1992 | Suthanthiran et al. . | |
| 5,176,617 | 1/1993 | Fischell et al. | 600/3 |
| 5,183,455 | 2/1993 | Hayman et al. | 600/7 |
| 5,199,939 | 4/1993 | Dake et al. | 600/3 |
| 5,203,772 | 4/1993 | Hammerslag et al. | 604/95 |
| 5,213,561 | 5/1993 | Weinstein et al. | 600/3 |
| 5,242,394 | 9/1993 | Tremulis | 604/95 |
| 5,267,960 | 12/1993 | Hayman et al. | 604/106 |
| 5,282,781 | 2/1994 | Liprie | 600/3 |
| 5,295,995 | 3/1994 | Kleiman | 606/194 |
| 5,302,168 | 4/1994 | Hess | 600/3 |
| 5,308,356 | 5/1994 | Blackshear, Jr. et al. | 606/194 |
| 5,344,383 | 9/1994 | Liping . | |
| 5,346,508 | 9/1994 | Hastings | 600/505 |
| 5,354,257 | 10/1994 | Roubin et al. . | |
| 5,370,685 | 12/1994 | Stevens . | |
| 5,385,152 | 1/1995 | Abele et al. | 600/585 |
| 5,391,139 | 2/1995 | Edmundson . | |
| 5,395,300 | 3/1995 | Liprie | 600/3 |
| 5,405,309 | 4/1995 | Carden, Jr. . | |
| 5,409,015 | 4/1995 | Palmero | 600/585 |
| 5,411,466 | 5/1995 | Hess | 600/3 |
| 5,425,720 | 6/1995 | Rogalsky et al. . | |
| 5,429,582 | 7/1995 | Williams . | |
| 5,484,384 | 1/1996 | Fearnot . | |
| 5,498,227 | 3/1996 | Mawad . | |
| 5,503,613 | 4/1996 | Weinberger | 600/3 |
| 5,503,614 | 4/1996 | Liprie | 600/7 |
| 5,520,194 | 5/1996 | Miyata et al. . | |
| 5,532,122 | 7/1996 | Drukier . | |
| 5,538,494 | 7/1996 | Matsuda . | |
| 5,540,659 | 7/1996 | Teirstein | 604/104 |
| 5,556,389 | 9/1996 | Liprie . | |
| 5,575,749 | 11/1996 | Liprie . | |
| 5,605,530 | 2/1997 | Fischell et al. . | |
| 5,611,767 | 3/1997 | Williams . | |
| 5,616,114 | 4/1997 | Thornton et al. . | |
| 5,618,266 | 4/1997 | Liprie . | |
| 5,624,372 | 4/1997 | Liprie . | |
| 5,643,171 | 7/1997 | Bradshaw et al. | 600/1 |
| 5,649,924 | 7/1997 | Everett et al. . | |
| 5,653,683 | 8/1997 | D'Andrea . | |
| 5,662,580 | 9/1997 | Bradshaw et al. . | |
| 5,674,177 | 10/1997 | Hehrlein et al. . | |
| 5,683,345 | 11/1997 | Waksman et al. . | |
| 5,688,220 | 11/1997 | Verin et al. . | |
| 5,707,332 | 1/1998 | Weinberger . | |
| 5,720,717 | 2/1998 | D'Andrea . | |
| 5,722,984 | 3/1998 | Fischell et al. . | |
| 5,728,042 | 3/1998 | Schwager . | |
| 5,730,698 | 3/1998 | Fischell et al. . | |
| 5,782,740 | 7/1998 | Schneiderman . | |
| 5,782,742 | 7/1998 | Crocker et al. . | |
| 5,795,286 | 8/1998 | Fischell et al. . | |
| 5,800,333 | 9/1998 | Liprie . | |
| 5,803,895 | 9/1998 | Kronholz et al. . | |
| 5,807,231 | 9/1998 | Liprie . | |
| 5,816,259 | 10/1998 | Rose . | |
| 5,816,999 | 10/1998 | Bischoff et al. . | |
| 5,820,553 | 10/1998 | Hughes . | |
| 5,833,593 | 11/1998 | Liprie . | |
| 5,840,008 | 11/1998 | Klein et al. . | |
| 5,840,009 | 11/1998 | Fischell et al. . | |
| 5,840,064 | 11/1998 | Liprie . | |
| 5,843,163 | 12/1998 | Wall . | |
| 5,851,171 | 12/1998 | Gasson . | |
| 5,851,172 | 12/1998 | Bueche et al. . | |
| 5,855,546 | 1/1999 | Hastings et al. . | |
| 5,857,956 | 1/1999 | Liprie . | |
| 5,863,284 | 1/1999 | Klein . | |
| 5,863,285 | 1/1999 | Coletti . | |
| 5,865,720 | 2/1999 | Hastings et al. . | |
| 5,871,436 | 2/1999 | Eury . | |
| 5,871,437 | 2/1999 | Alt . | |
| 5,873,811 | 2/1999 | Wang et al. . | |
| 5,879,282 | 3/1999 | Fischell et al. . | |
| 5,882,290 | 3/1999 | Kume . | |
| 5,882,291 | 3/1999 | Bradshaw et al. . | |
| 5,891,091 | 4/1999 | Teirstein . | |
| 5,897,573 | 4/1999 | Rosenthal et al. . | |
| 5,899,882 | 5/1999 | Waksman et al. . | |

FOREIGN PATENT DOCUMENTS

| | | |
|---|---|---|
| 0 749 764 A1 | 12/1996 | European Pat. Off. . |
| 0 754 472 A2 | 1/1997 | European Pat. Off. . |
| 0 754 473 A2 | 1/1997 | European Pat. Off. . |
| 0 593 136 B1 | 3/1997 | European Pat. Off. . |
| 0 778 051 A1 | 6/1997 | European Pat. Off. . |
| 0 801 961 A2 | 10/1997 | European Pat. Off. . |
| 0 813 894 A2 | 12/1997 | European Pat. Off. . |
| 0 629 380 B1 | 7/1998 | European Pat. Off. . |
| 1065989 | 9/1959 | Germany . |
| 3620123 A1 | 12/1987 | Germany . |
| 91 02 312 U | 8/1992 | Germany . |
| 195 26 680 A1 | 1/1997 | Germany . |
| 197 54 870 A1 | 8/1998 | Germany . |
| 197 24 233 C1 | 12/1998 | Germany . |
| WO 86/03124 | 6/1986 | WIPO . |
| 86/04248 | 7/1986 | WIPO . |
| 9200776 | 1/1992 | WIPO . |
| 92/03179 | 3/1992 | WIPO . |
| 93/04735 | 3/1993 | WIPO . |
| 94/16646 | 8/1994 | WIPO . |
| WO 94/25106 | 11/1994 | WIPO . |
| WO 94/26205 | 11/1994 | WIPO . |
| WO 95/07732 | 3/1995 | WIPO . |
| 95/30384 | 11/1995 | WIPO . |
| 9606654 | 3/1996 | WIPO . |
| WO 96/06654 | 3/1996 | WIPO . |
| WO 96/10436 | 4/1996 | WIPO . |
| 9613303 | 5/1996 | WIPO . |
| WO 96/13303 | 5/1996 | WIPO . |
| WO 96/14898 | 5/1996 | WIPO . |
| 96/17654 | 6/1996 | WIPO . |
| WO 96/22121 | 7/1996 | WIPO . |
| WO 96/29943 | 10/1996 | WIPO . |
| WO 96/40352 | 12/1996 | WIPO . |
| WO 97/07740 | 3/1997 | WIPO . |
| WO 97/09937 | 3/1997 | WIPO . |
| WO 97/18012 | 5/1997 | WIPO . |
| WO 97/19706 | 6/1997 | WIPO . |
| WO 97/25102 | 7/1997 | WIPO . |
| WO 97/25103 | 7/1997 | WIPO . |
| WO 97/40889 | 11/1997 | WIPO . |
| WO 98/01183 | 1/1998 | WIPO . |
| WO 98/01184 | 1/1998 | WIPO . |
| WO 98/01185 | 1/1998 | WIPO . |
| WO 98/01186 | 1/1998 | WIPO . |
| WO 98/11936 | 3/1998 | WIPO . |
| WO 98/16151 | 4/1998 | WIPO . |
| WO 98/20935 | 5/1998 | WIPO . |
| WO 98/25674 | 6/1998 | WIPO . |
| WO 98/29049 | 7/1998 | WIPO . |
| WO 98/30273 | 7/1998 | WIPO . |
| WO 98/34681 | 8/1998 | WIPO . |
| WO 98/36788 | 8/1998 | WIPO . |
| WO 98/36790 | 8/1998 | WIPO . |
| WO 98/36796 | 8/1998 | WIPO . |
| WO 98/39052 | 9/1998 | WIPO . |
| WO 98/39062 | 9/1998 | WIPO . |
| WO 98/39063 | 9/1998 | WIPO . |
| WO 98/40032 | 9/1998 | WIPO . |
| WO 98/46309 | 10/1998 | WIPO . |
| WO 98/55179 | 12/1998 | WIPO . |
| WO 98/57706 | 12/1998 | WIPO . |
| WO 99/01179 | 1/1999 | WIPO . |
| WO 99/02219 | 1/1999 | WIPO . |
| WO 99/04706 | 2/1999 | WIPO . |
| WO 99/04856 | 2/1999 | WIPO . |
| WO 99/10045 | 3/1999 | WIPO . |

OTHER PUBLICATIONS

Lommatzsch et al., "Radiation effects on the optic nerve observed after brachytherapy of choroidal melanomas with 106Ru/106Rh plaques", *Graefe's Arch. Clin. Exp. Ophthalmology* vol. 232, pp. 482–487, 1994.

*Radiotherapy of Intraoculare and Orbital Tumors,* Springer–Verlak publishers, Berlin Heidelberg and New York, copyright 1993, pp. 23–30 and 363–367.

Fackelmann, "Harbinger of a Heart Attack", *Science News,* vol. 151, Jun. 14, 1997, pp. 374–375.

Raloff, "Nuclear Medicine Gets Friendlier—Experimental Therapies Seek to Posion Just the Disease", *Science News,* Bol. 152, Jul. 19, 1997, pp. 40–41.

Sutherland, "Managing Cancer Through Synergy", *Administrative Radiology Journal,* Nov. 1996, pp. 21–27.

Novoste IDE For Anti–Restenosis Endovascualr Beta Radiation System, MDDI Reports, 2 pages (May 22, 1995).

Inhibition by Irradiation of Smooth Muscle Cell Proliferation in the de–endothelialized Rat Aorta, Z. Weshler, M.S., et al., Frontiers in Radiation Biology, Proceedings of the 21st Annual Meeting of the European Society for Radiation Biology, Tel Aviv, pp. 133–138, (Oct. 1988).

Effect of Iridium 192 Radiation on Thromboatherosclerotic Plaque in the Rabbit Aorta, M. Friedman, M.D., et al., Arch Path, vol. 80, pp. 285–290, (Sep. 1965).

Fractionated Brachytherapy: Catheter Insertion and Dosimetry, P. L. Gildenberg, et al., Proceedings of the XIth Meeting of the World Society for Stereotactic and Functional Neurosurgery, Ixtapa, Mexico, pp. 246–249, (Oct. 11–15, 1993).

Role of Ionizing Irradiation For 393 Keloids, T. L. Borok, M.D., et al., International Journal of Radiation Oncology Biol. Phys., vol. 15, pp. 865–870, (Oct. 1988).

Mechanism of Angioplasty and Its Relation to Restenosis, David P. Faxon, M.D., et al., Am. Journal of Cardiology, vol. 60, pp. 114–118, (1987).

Percutaneous Transluminal Coronary Angioplasty, Spencer B. King III, M.D., et al., Coronary Arteriography and Angioplasty, Chapter 17, pp. 433–460, (on or before 1985).

Endovascular Afterloading with 192 Iridium HDR in the Treatment of Recurrent Intimal Hyperplasia in Stented Peripheral Arteries, D. Liermann, M.D., Ph.D., et al., Stents—State of the Art and Future Developments, Boston Scientific Corporation, pp. 299–314, (1995).

Gammamed 926.100, Esophagus Applicator, (Specification, 1 page), Isotopen–Technik Dr. Sauerwein Gmbh, (Jan. 1990).

Gammamed 926.120, Centering Intra–Luminal Applicator, (Specification, 1 page), Isotopen–Technik Dr. Sauerwein Gmbh, (Jan. 1990).

Nitinol . . . The Material of Choice for Safer, More Effective Medical Procedures, FlexMedics Corporation, 3 pages, (1989).

Mechanisms of Stenosis after Arterial Injury, A. W. Clowes, et al., Laboratory Investigation vol. 49, No. 2, pp. 208–215, 1983.

Prevention of restenosis after percutaneous transluminal coronary angioplasty: The search for a "magic bullet", W. Hermans, M.D., et al., American Heart Journal, vol. 122, No. 1, pp. 171–187, Jul. 1991.

Restenosis After Coronary Angioplasty: A Multivariate Statistical Model to Relate Lesion and Procedure Variables to Restenosis, J. W. Hirshfeld, Jr., M.D., FACC, et al:, JACC, vol. 18, No. 3, pp. 647–656, Sep. 1991.

Novel Approach to the Analysis of Restenosis After the Use of Three New Coronary Devices, R. E. Kuntz, M.D., MS, et al., JACC, vol. 19, No. 7, pp. 1493–1499, Jun. 1992.

Radiosensitivity of Vascular Tissue—II. Differential Radiosensitivity of Aortic Cells In Vitro, K. Fischer–Dzoga, et al., Radiation Research 99, pp. 536–546, 1984.

Low–Dose Irradiation Inhibits Clonal Proliferation Of Smooth Muscle Cells: A New Approach to the Prevention of Restenosis?, T. A. Fischell et al., Arteriosclerosis Council Abstracts, p. 1435a, 1991.

Effects of Radiation on the Microvasculature—Implications for Normal–Tissue Damage, J. W. Hopewell, et al., Radiation Tolerance of Normal Tissues, Front Radiat Ther Oncol, vol. 23, pp. 85–95, 1989.

Gamma Irradiation Inhibits Neointimal Hyperplasia in Rats After Arterial Injury, S. Shimotakahara, MD, et al., Stroke, vol. 25, No. 2, pp. 424–428, Feb. 1994.

Radiation Therapy Following Keloidectomy: A 20–Year Experience, J. J. Kovalic, M.D., et al., Int J Radiation Oncology Biol Phys, vol. 17, No. 1, pp. 77–80, Jul. 1989.

The Treatment of 783 Keloid Scars by Iridium$^{192}$ Interstitial Irradiation After Surgical Excision, A. Escarmant, M.D., et al., Int J Radiation Oncology Biol Phys, vol. 26, No. 2, pp. 245–251, 1993.

Management of Pterygium with Surgery and Radiation Therapy, S. B. Paryani, M.D., et al., Int J Radiation Oncology Biol Phys, vol. 28, No. 1, pp. 101–103, 1994.

Pterygium Treated with Excision and Postoperative Beta Irradiation, R. B. Wilder, M.D., et al., Int J Radiation Oncology Biol Phys, vol. 23, No. 3, pp. 533–537, 1992.

Prevention of Heterotopic Ossification with Irradiation after Total Hip Arthroplasty, V. D. Pellegrini, M.D., et al., The Journal of Bone and Joint Surgery, vol. 74–A, No. 2, pp. 186–200, 1992.

The Antiatherogenic Effect of Iridium$^{192}$ upon the Cholesterol–fed Rabbit M. Friedman, et al., Journal of Clinical Investigation, vol. 43, No. 2, pp. 185–192, 1964.

Comparative Effects of Single and Fractionated Doses of Irradiation Upon Smooth Muscle Cell Proliferation, M.A. Abbas, et al., Clinical Research, vol. 40, No. 1, p. 43A (Abstract), 1992.

Intracoronary Irradiation Markedly Reduces Neointimal Proliferation After Balloon Angioplasty in Swine: Persistent Benefit at 6–Month Follow–Up, J. G. Wiedermann, M.D., et al., JACC, vol. 25, No. 6, pp. 1451–1456, May 1995.

Endovascular Irradiation–A New Method To Avoid Recurrent Stenosis After Stent Implantation In Peripheral Arteries: Technique And Preliminary Results, H. D. Böttcher, M.D., et al., Int J Radiation Oncology Biol Phys, vol. 29, No. 1, pp. 183–186, purportedly presented at the 34th Annual ASTRO Meeting in San Diego, CA, Nov. 1992, published 1994.

Prophylactic Endovascular Radiotherapy to Prevent Intimal Hyperplasia after Stent Implantation in Femoropopliteal Arteries, D. Liermann, et al., Cardiovasc Intervent Radiol, vol. 17, pp. 12–16, 1994.

Low–Dose, β–Particle Emmission From 'Stent' Wire Results in Complete, Localized Inhibition of Smooth Muscle Cell Proliferation, T. Fischell, M.D., et al., Basic Science Reports, Circulation, vol. 90, No. 6, pp. 2956–2963, Dec. 1994.

Feasibility of Intracoronary β–Irradiation To Reduce Restenosis After Balloon Angioplasty: A Clinical Pilot Study, V. Verin, M.D., et al., Circulation, vol. 95, No. 5, pp. 1138–1144, Mar. 1997.

Coronary Artery Disease Following Mediastinal Radiation Therapy, L. Annest, M.D., et al., The Journal of Thoracic and Cardiovascular Surgery, vol. 85, No. 2, p. 257–263, Feb. 1983.

Cardiac Disease After Mediastinal Irradiation for Seminoma, G. Lederman, M.D., et al., Cancer, vol. 60, No. 4, pp. 772–776, Aug. 15, 1987.

Catheter–Based Radiotherapy To Inhibit Restenosis After Coronary Stenting, P. S. Teirstein, M.D., et al., The New England Journal of Medicine, vol. 336, No. 24, pp. 1697–1703, Jun. 12, 1997.

Effects of High Dose Intracoronary Irradiation on Vasomotor Function and Smooth Muscle Histopathology, Joseph G. Wiedermann, M.D., et al., Oct. 1992.

Intracoronary Irradiation Markedly Reduces Restenosis after Balloon Angioplasty in a Porcine Model, Joseph G. Wiedermann, M.D., et al., Oct. 1993.

U.S. Application No. 08/489,464, entitled "A Medical Appliance For Treatment By Ionizing Radiation," filed Jun. 12, 1995, which is commonly owned by the assignee of the above–captioned application.

U.S. Application No. 08/581,098, entitled "A Medical Appliance For Ionizing Radiation Treatment," filed Dec. 29, 1995, which is commonly owned by the assignee of the above–captioned application.

"Strontium—90—Applikator für interstitielle Bestrahlung der Hypophyse," Fortschritte auf dem Begiete der Röntgenstrahlen und den Nuklearmedizin, Holmer et al., pp. 524–578 (1967), with English translation.

JACC vol. 21 No. 2, 889–25, "Suppression of Intimal Proliferation after Balloon Angioplasty with Local Beta Irradiation in Rabbits," Shefer et al. (Feb. 1993).

International Journal of Radiation Oncology Biology Physics, vol. 24, Supplement 1, p. 171, "Prophylaxis of Intimal Hyperplasia after Stent–Implantation in Peripheral Arteries Using Endovascular Irradiation," Böttcher et al. (1992).

Introduction to Modern Physics, F. K. Richtmyer et al., 5th Edition, 1955. p. 584.

The Atomic Nucleus, Robley D. Evans, Ph.D., Massachusetts Institute of Technology, 1955.

Search Report in corresponding European patent application serial No. EP 93110531.6, dated Dec. 14, 1993, together with Communication and one–page Annex.

Proliferation Studies of the Endothelial and Smooth Muscle Cells of the Mouse Mesentery After Irradiation, D. G. Hirst et al., Gray Laboratory of the Cancer Research Campaign, Mount Vernon Hospital, Norwood, Middlesex, Cell Tissue Kinet. (1980) 13, pp. 91–104.

Intra–arterial Beta Irradiation Prevents Neointimal Hyperplasia in a Hypercholesterolemic Rabbit Restenosis Model, Vitali Vernin and Youri Popowski (co–inventors of the above–captioned application) et al., 1995 American Heart Association, Inc.

High Dose Rate Brachytherapy for Prevention of Restenosis After Percutaneous Transluminal Coronary Angioplasty: Preliminary Dosimetric Tests of a New Source Presentation, Youri Popowski and Vitali Vernin (co–inventors of the above–captioned application) et al., accepted for publication Feb. 24, 1995, Int. J. Radiation Oncology Biol. Phys., vol. 33, No. 1, pp. 211–215, 1995.

Intra–Arterial $^{90}$Y Brachytherapy: Preliminary Dosimetric Study Using a Specially Modified Angioplasty Balloon, Youri Popowski and Vitali Vernin (co–inventors of the above–captioned application) et al., Int. J. Radiation Oncology Biol. Phys., vol. 33, No. 3, pp. 713–717, 1995.

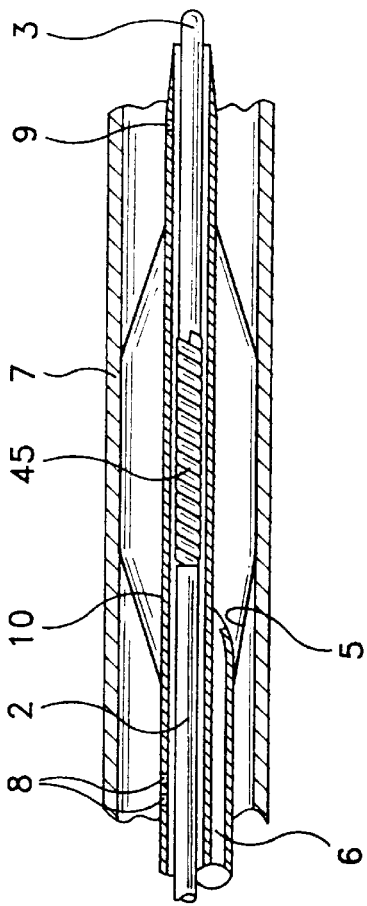
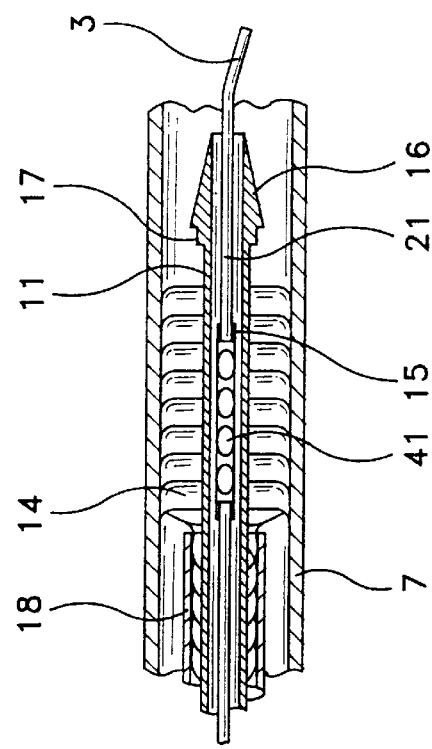
FIG-3
FIG-4

MEDICAL APPLIANCES FOR THE TREATMENT OF BLOOD VESSELS BY MEANS OF IONIZING RADIATION

BACKGROUND OF THE INVENTION

This invention relates to a medical appliance for the treatment of a portion of blood vessel by means of ionizing radiation, comprising a catheter for percutaneous transluminal treatment of the blood vessel, an inflatable dilatation balloon surrounding the catheter, a radioactive radiation emitter, and means for advancing, and removing, the radioactive radiation emitter into, and from, the portion of the blood vessel, respectively it relates to a medical appliance for the treatment of a portion of blood vessel by means of ionizing radiation, comprising a catheter defining a perfusion channel, a radioactive radiation emitter, and means for advancing, and removing the radioactive radiation emitter into, and from, the portion of the blood vessel.

Atherosclerosis causes thickening and hardening of arteries and formation of deposits of plaque or plaque-ridden tissue within the arterial lumen. Such a disease is commonly treated by means of percutaneous transluminal angioplasty techniques involving, inter alia, the non-surgical widening of a passage through an artery by means of a balloon inflated to dilate the area of obstruction or the abrasion of the deposit by means of atherectomy. Unfortunately, the major limitation of these angioplasty or atherectomy techniques is the relatively important rate of restenosis. As it has been shown, the balloon angioplasty produces intimal and medial injury leading to excessive platelet aggregation and cell mediators activation followed by an elevated production of myocital growth factors. The cascade of these events, regulated by arterial wall cells nuclei, results in hyperproliferation of smooth muscle cells and migration of myocites and macrophages from the media layer towards the intima and further accelerates excessive neo-intimal formation leading to lumen narrowing. Many approaches to prevent this phenomenon have been tested, among which regimes of anticoagulation, antiplatelet therapy, vasodilators, and serum cholesterol level reducers, however, without appreciable therapeutic effect. As a further approach to this problem, it has been found that ionizing radiation could prove helpful in the treatment of unwanted cell proliferation which causes recurrent stenoses or occlusion after angioplasty.

The document International Journal of Radiation Oncology Biology Physics, Vol. 24 Suppl. 1, page 171, which reports Proceedings of the 34th Annual ASTRO Meeting of November 1992, refers to a study on the prophylaxis of intimal hyperplasia after stent implantation in peripheral arteries using endovascular irradiation. This study was directed to the frequency of recurrent stenoses or occlusions following stent implantation in peripheral arteries due to rapid intimal hyperplasia. To stop the proliferation of connective tissue an endovascular brachytherapy treatment was performed after percutaneous transluminal angioplasty. The method describes stent implantation after recanalization done by percutaneous transluminal angioplasty, and placing of a 10 Ci Iridium gamma irradiation source into the implanted stent. No specific measures are described which would ensure circumferentially uniform radiation impact on the vessel wall. In this study the radial position of the irradiation source inside the stent was determined by gravity.

The document JACC Vol. 21 N° 2, February 1993: 185A, reports a study of the effects of locally delivered ionizing radiation on the proliferation response to balloon over-stretching injury. The injury model was balloon angioplasty of the central artery of the ear of rabbit and the ionizing radiation was delivered as high energy beta from a sealed SR90 source in a single dose (skin dose of 900 rad) after a scheduled time delay from the injury. The document further refers to a second protocol using porcine coronary injury model with transluminal intravascular irradiation. This publication does not disclose any specific measure to ensure an evenly distributed radiation in the vessel. U.S. Pat. No. 5,147,282 discloses a manual irradiation loading apparatus particularly suitable for intrabronchial and gynecological irradiation treatment. The apparatus comprises a lead or equivalent radiation shielding body with a longitudinally extending cable receiving passage therein. A cable having radioactive seeds provided on one end thereof is received in the cable-receiving passage. During storage, the portion of the cable bearing the radioactive source is located in the cable-receiving passage within the shielding body. During use, a catheter placed in a patient is joined to the shielding body and the portion of the cable bearing the radioactive source material is advanced through the cable-receiving passage in the shielding body and into the catheter. The radioactive seeds are slidingly positioned inside the catheter, however the radial position of the catheter within the vessel is not controlled.

U.S. Pat. No. 4,588,395 describes, i.a., a catheter device for generating radioactive radiation into an artery for medicinal or repair purposes. This device comprises a catheter the tubular wall of which is collapsed at its distal end to form a sealing interface closing off the interior volume. Within this volume is located a sort of radioactive pill which can be urged forwardly by a piston connected to a flexible shaft controlled at the proximal end of the catheter, forward motion of the piston forcing the pill through the sealing interface in order to protrude from the distal end of the catheter and affect the artery. No means are provided with this catheter to secure a certain predetermined orientation of this catheter inside the geometry of the vessel section.

In addition to irradiation external to the site, the document WO 93/04735 also describes an apparatus for the treatment of an artery, comprising a radioactive dose and a means operatively connected to such a radioactive dose to bring it into a selected region of an artery. In a first embodiment, the apparatus comprises a sheath removably positioned over a windowed housing containing a radioactive dose and connected to a catheter shaft, whereby the relative motion between catheter shaft and sheath permits moving the windowed housing in and out of the sheath, thereby exposing the radioactive dose which may affect the selected place in the artery. In a second embodiment, the device comprises a catheter shaft surrounded by an angioplasty balloon on the outer surface of which are affixed radioactive elements intended to be forced into contact with the artery wall upon inflation of the balloon. The balloon has a perfusion channel to allow perfusion of blood e.g., from proximal of the balloon to distal of the balloon. Perfusion of blood is therefore possible even during the phase when the balloon is inflated and normal blood flow is interrupted. A third embodiment, substantially similar to the first one, includes a sheath intended to provide a shielding to a radioactive dose and a motion wire to provide slidable motion of the radioactive dose within the sheath. A fourth embodiment comprises an inflatable stent delivery balloon for expansion of a stent to which a radioactive dose is associated as a cladding, a coating or an additive within the stent material itself. A fifth embodiment shows a shrinkable tubing attached to a catheter shaft and a plurality of radioactive seeds located in the tubing where they are separated from each other by heat shrinking of the tubing which therefore encapsulates the seeds.

The sheath configuration of the first embodiment suffers from the same drawbacks as the configuration known from the previously mentioned publications. The radial orientation of the radioactive dose inside the vessel is determined by gravity. In the second embodiment, the radioactive elements affixed to the balloon and forced into contact with the artery wall, the radioactive elements provide uniform radiation impact on the artery wall only as far as specifically the area of the individual radioactive element is concerned. A circumferentially uniform radiation on the artery wall is not possible with this configuration. Besides that, the radioactive elements on the outer surface of the balloon are difficult to secure on the flexible balloon surface. Their fixture would have to meet severe safety requirements against loss under all conditions. This would lead to some specific complications. Finally radioactive elements and the fixture of these elements add unfavorably to the deflated profile of the balloon to pass through tight stenoses. The third embodiment with the slidable radioactive dose within the sheath shows the same problem as the first embodiment. It shows no means to control the transversal orientation of the sheath in the vessel. The fourth embodiment, the cladded expanding stent, represents regarding uniformity of radiation the same unfavorable situation as the configuration of the balloon with affixed radioactive elements. Finally, the fifth embodiment adds nothing to the solution of the positioning problem, it mainly refers to the problem of how to safely secure the radioactive seeds to a catheter shaft.

In all these devices, the radiation cannot be uniform, either because there is absolutely no possibility of having the radioactive element correctly positioned within the artery, or because the radioactive element irregularly bears against the vessel wall.

The document DE 3620123-A1 discloses an apparatus for measuring and irradiating body cavities which permits the placing and positioning of a light conductor at the center of a cavity in order to achieve homogeneous lighting thereof via a dispersing agent. To this effect, a light conductor is located in a tubular catheter surrounded by two optically transparent centering flexible balloons at a distance from each other and which are inflated by a dispersing agent in order to have them rest against the wall of the body cavity. The portion of the catheter which is located between the balloons is stiffer than the rest of the catheter to avoid modification of the distance between the two balloons, for instance due to curving of the catheter. The system is said to be usable for a blood vessel, but the system needs a dispersing agent and two balloons proximal and distal of the radiation source to accommodate the dispersing agent between the balloons. The two balloons are occlusion balloons. Occlusion balloons have to be resilient to safely fulfill their task in a vessel of unknown exact shape and size. Because of this resiliency, occlusion balloons can not be used simultaneously as dilatation balloons. Resilient balloons would overstretch the vessel wall when used with the higher pressures that are required for a successful angioplasty. Of course the doctor has control over the inflation pressure with resilient balloons same as with dilatation balloons, but this is not sufficient for safe angioplasty. With a resilient balloon the doctor has no control over the inflated diameter or over the shape to which the balloon is inflated.

SUMMARY OF THE INVENTION

The purpose of this invention is to improve the conditions of radioactive radiation treatment of blood vessels stenoses due to excessive intimal formation by proposing a medical appliance with dilatation balloon or with perfusion channel for a vessel wall radiation which is uniform around the circumference of the vessel, an appliance that is simple to manufacture and easy to use, that allows traversal of narrow stenoses and that allows safe securing of the radioactive emitter to its advancing and removing means.

To this effect, the invention complies with the definitions given in the claims.

In that way, it becomes possible to improve dosage control of the radioactive radiation with regard to distance between the radioactive source and the vessel wall, respectively with regard to distance between radioactive source and vessel wall and timing during which the radioactive treatment has to be applied.

Specifically the essentially centered emitter ensures essentially equal radial distance to all segments of the vessel wall so that a pattern of areas with overdosage because of too narrow distance and areas with underdosage because of too wide distance to the vessel wall is avoided. The impact of radiation on the vessel wall is circumferentially essentially uniform.

If the medical appliance comprises a dilatation balloon, dilatation and radioactive treatment can be performed in one procedure. The cure of the vessel wall proliferation can be taken immediately with the cause for the vessel wall proliferation. This also has the advantage of an optimum automatic match between the location in the vessel where the cure is taken and the location in the vessel where the cause is laid. If during the procedure the dilatation balloon is not shifted inside the vessel, the radiation treatment will automatically be in the exact place where it is needed, unintentional exposure of undilated vessel portions to radiation is reduced.

If the medical appliance comprises a perfusion channel, the blood flow in the radiated vessel is not totally cut off during the time of exposure to radiation. That means, that ischemia in the areas lying in the blood flow direction behind the treatment site and the dangerous consequences of ischemia for example in coronary arteries are reduced. The radiation can with a perfusion channel be extended longer without these negative consequences and that again allows the use of an emitter with relatively low radiation density which will have less unintended side effects during the rest of the treatment procedure.

If the centered emitter is movable within the catheter, this allows specifically a quick and safe method of use for the appliance. The emitter then can be traversed to the place of treatment simply by sliding it forward inside the catheter. This ensures an easy and quick handling of the device and specifically makes sure that the vessel path from the percutaneous vessel entrance to the exact position of the treatment place is not unintentionally overexposed to radiation due to slow advance speed of the emitter and that the exact exposure time for the radiation at the treatment site can reliably be observed. Also the vessel wall is saved from unnecessary mechanical stress from the advancement of the device. The potentially time consuming exact location of the treatment site with the medical appliance within the branched vessel system is in this case not done under radiation.

Preferably the radioactive radiating emitter is selected from the group of beta emitters. Beta emitters have a relatively short half-life. This is desirable to allow procedure times that are manageable in interventional medicine. Also the high radiation activity per specific gravity of beta emitters leads to small dimensions for the emitter which is very important in interventional techniques. Furthermore the travel distance of beta radiation inside the tissue is very short. This is very favorable for the treatment here in question. To interrupt the mechanism that lead to tissue proliferation, radiation of the surface of the vessel wall is sufficient. Radiation that travels deep into the tissue is undesirable and induces side effects. Furthermore, beta radiation needs no heavy shielding like lead or concrete. A beta radiation emitter can be shielded with plastic shieldings of practicable thicknesses so that beta emitters can be transported and handled with relatively low additional safety precautions compared to usual non-radiating products and shielded beta emitters are not bulky or heavy. Specifically the treatment room where the procedure is carried out needs no specific reinforcement in concrete, lead or other material. It is practically most important, that with the use of beta emitters the doctor can stay in the room where the treatment is made, he can directly carry out the treatment. The use of beta emitters therefore allows this treatment to be implemented in any arbitrary hospital without specific prior local precautions at the hospital itself.

The use of an emitter in form of a filament has the advantage, that the emitter can be safely fixed to the positioning means within the risk of any part of the emitter getting lost or without the risk of a container becoming untight, being thus safer than seeds or powder or other forms. In addition, a further advantage of the filament is dense concentration of dose in small diameter.

Preferably the beta emitter is of 90 Yttrium which has a halflife of 2.7 days, a middle energy 0.942 Mev and maximal energy of 2.28 Mev, which would allow appreciable irradiation within a short distance from the filament, whereby only the internal layers of the vessel wall will be heavily irradiated while the more external structures will receive a dose which decreases with the square of the distance. Yttrium can be made available in form of filaments, so that with the selection of Yttrium the advantages of beta emitters and of filament emitters are available.

Because of its mechanical characteristics, the filament of 90 Yttrium can have a diameter equal to or less than 0.9 mm. An emitter of this dimension is specifically suitable for percutaneous transluminal procedures.

Subject to a heat elaboration under vacuum to avoid rapid oxidation and the resulting risk of breaking, the filament of 90 Yttrium can even have a diameter equal or less than 0.2 mm. An emitter of this dimension can be introduced into the guidewire lumen of such percutaneous transluminal devices that have a very small deflated or folded profile. Such devices can use introducer sets with small outer diameter and low trauma at the percutaneous introduction site and inside the vessel such devices can cross very narrow stenoses.

If the emitter is coiled around the guide wire, this has the advantage, that an easy to accomplish and safe fixture is achieved. It can be made in a simple procedure, which is possible even under shielding conditions and thus can be made after the emitter has been activated. This is advantageous because a fixture to the guide wire before the activation of the emitter brings the problem of partially activating the guide wire together with the activation of the already affixed emitter.

Even only partly activation of the guide wire material might induce already unfavorable effects in this material, e.g., gamma radiation.

A preferred approach is to make use of a guide wire of titanium which, after activation in a powerful field of neutrons, will have a decay time of 5.8', and will advantageously solve the problem of undesirable long living of isotopes induction in other guide wires while providing mechanical qualities equivalent to those of stainless steel. Therefore with a titanium wire as carrier for the emitter, the emitter can be affixed to the carrier before the emitter is activated without any practical risk of radiation pollution. This brings the great advantage that the affixing procedure can be made under normal conditions without any radioactive shielding for the involved persons. Also in this configuration the emitter needs not to be separated again from the guide wire for reactivation of the emitter when the activity of the emitter is consumed.

These and other objects will become readily apparent from the following detailed description with reference to the accompanying drawings which show, diagrammatically and by way of example only, six embodiments of the invention.

BRIEF DESCRIPTION OF THE DRAWINGS

FIG. 3 is an axial cut of the third embodiment.

FIG. 4 is an axial cut of the fourth embodiment.

DETAILED DESCRIPTION OF THE INVENTION

In all the embodiments, only the portions which have to be located in a blood vessel stenosis have been depicted; the other portions of the embodiments shown may be devised as currently practiced in the art. Similarly, no particular shielding equipment for storage and transit of radioactive materials is being discussed here, reference being solely made in this respect to known techniques such as for instance those described in U.S. Pat. No. 5,147,282.

Figure 1:
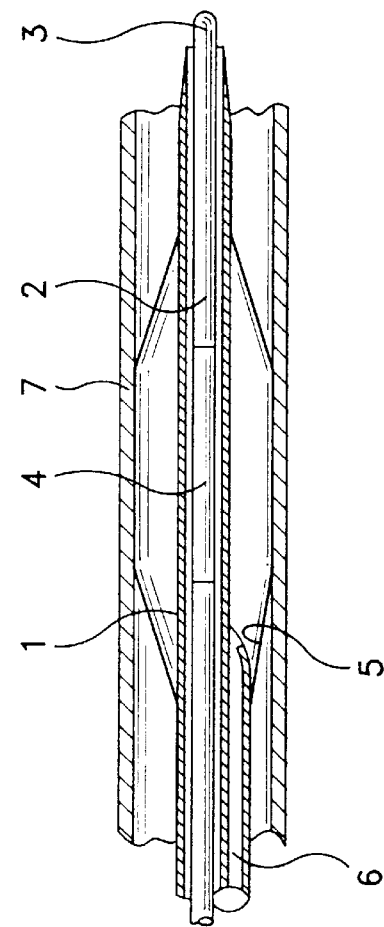
FIG. 1 is an axial cut of the first embodiment.

The first embodiment of FIG. 1 comprises a flexible catheter tube 1 in which is centered a guide wire 2 with a tip 3, said guide wire being in sliding fit within the catheter tube 1. A substantially cylindrical dilatation balloon 5 is mounted coaxially on the catheter tube 1 to which it is affixed annularly by its ends. The catheter 1 is a two lumen catheter in which the second lumen 6 acts as an inflation tube for the balloon 5. This balloon 5 is shown in inflated condition at the location of a stenosis (not shown) of a blood vessel 7, for instance a coronary artery. A radioactive radiation emitter in the form of a filament 4 is integrated into the guide wire 2 inside the balloon 5, this radioactive filament 4 being thus essentially centered in the balloon at the location of its dilatation in the blood vessel. The radioactive radiation of the filament 4 is thus applied uniformly to the dilated stenosis due to the centering achieved by the sole dilatation balloon 5, which would result in optimal dosimetric homogeneity of the irradiation procedure. The term essentially centered for the position of the emitter inside the balloon or inside the blood vessel is used in this document to describe configurations which in normal use do not lead to alternating segments along the vessel wall circumference with unsufficiently treated cell proliferation on one side and unnecessary radioactive overdoses on the other side. This use of the term essentially centered therefore includes configurations in which the emitter in use is secured in a predetermined position in the vessel section and in which this position is spaced from the vessel wall but in which the emitter is not held in the precise center of the medical device or the vessel section but is held somehow decentered and in which despite of such decentralization of the emitter, the treatment results that are achieved with the device are still satisfactory from a medical point of view.

Figure 2:
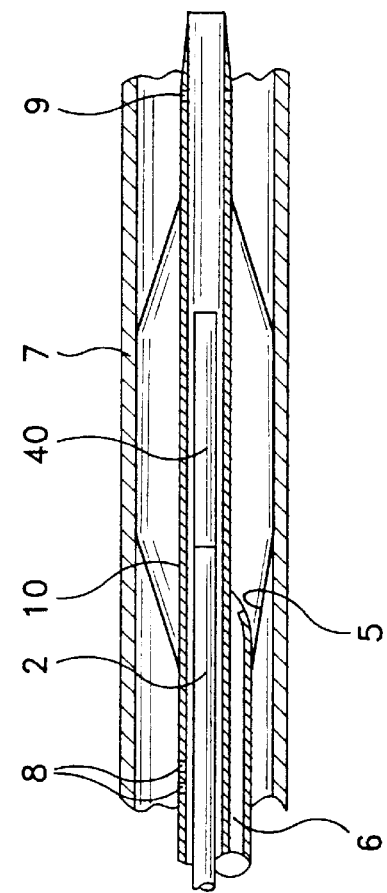
FIG. 2 is an axial cut of the second embodiment.

The embodiment of FIG. 2 comprises the basic configuration of the first embodiment of FIG. 1 with an added perfusion capacity via holes 8 and 9 respectively arranged in the wall of the catheter 10 before and after the balloon 5. The radioactive filament 40 is affixed to the distal end of the guide wire 2. In addition to the balloon centering and resulting uniform irradiation achieved by the embodiment of FIG. 1, this embodiment permits maintaining the irradiation for a substantially longer time as blood flow is no more hindered by the balloon. It also permits to place the radioactive emitter at the level of angioplasty without getting the distal part of the guide wire out of the catheter.

The embodiment of FIG. 3 combines the basic configurations of the embodiments of FIGS. 1 and 2 except that in this embodiment the filament 45 is coiled around the guide wire 2 to facilitate assembly thereof.

The fourth embodiment of FIG. 4 comprises a flexible catheter tube 11 in which is centered a guide wire 21 with a distal tip 3, said guide wire 21 being in sliding fit within the catheter tube. This catheter tube 11 comprises at its distal end a truncated cone head 16 having a rear rest shoulder 17 adapted to house the fore end of a tube 18 mounted in sliding fit over the catheter 11. This tube 18 is adapted to enclose and free by its relative motion with respect to the catheter the flexible bristles 14 of a brush coaxially mounted on and affixed to the catheter 11. Inside the catheter 11, at the location of the bristles 14, the guide wire 21 is interrupted and its two portions are interconnected by a tube 15 coaxial to the guide wire and in which are located radioactive seeds 41. By this configuration, upon introduction of the catheter 11 into a blood vessel 7 such as, for instance, a coronary artery, and backward motion of the tube 18 with respect to the catheter 11, the bristles 14 are freed and come to rest against the inner wall of the blood vessel, thereby centering the catheter 11 into the blood vessel. The radioactive radiation of the seeds 41 is thus uniformly applied to the vessel wall and timing of irradiation can be selected at will in view of the blood flow through the bristles. Upon forward motion of the tube 18 over the catheter 11, the bristles 14 are applied against the catheter 11 which can be then easily removed from the blood vessel.

Figure 5:
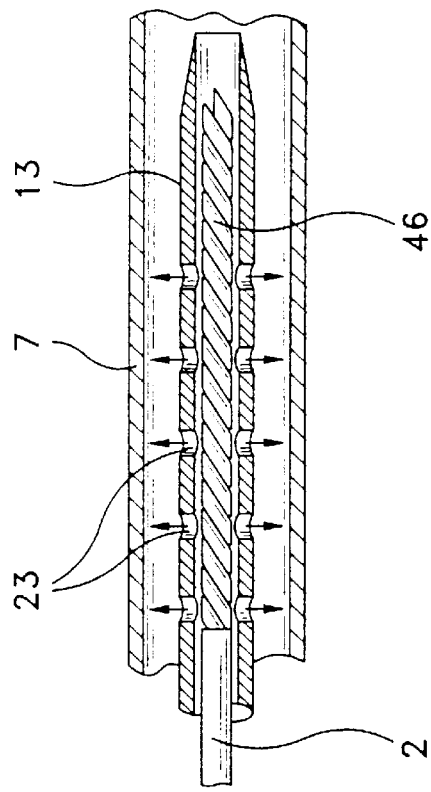
FIG. 5 is an axial cut of the fifth embodiment.

The embodiment shown in FIG. 5 comprises a flexible catheter tube 13 with a guidewire 2 centered in sliding fit therein as in the previous embodiments. The catheter 13 comprises a series of apertures 23 regularly spaced all around its distal portion and the inner channel of the catheter tube 13 is fed at its proximal end by a source of physiological solution under pressure (not shown). Inside the catheter tube, in the region of the apertures 23, a radioactive radiation emitter 46 in the form of a coiled filament is affixed to the distal portion of the guide wire 2. By this configuration, once the catheter has been introduced into a blood vessel 7 such as for instance a coronary artery, the source of physiological solution is activated, thereby feeding the inner channel and apertures 23 of the catheter 13. The physiological solution exits by the apertures 23 and creates a uniform jet pressure all around the catheter bumping against the vessel wall, thereby assuring centering of the catheter into the blood vessel. The radioactive radiation of the filament is thus uniformly applied against the vessel wall while blood flow is assured around the catheter, thereby permitting selection at will of irradiation time. As for the embodiment of FIG. 2, the assembly of the radioactive emitter at the distal end of the guide wire permits treatment without getting the distal part of the guide wire out of the catheter.

Figure 6:
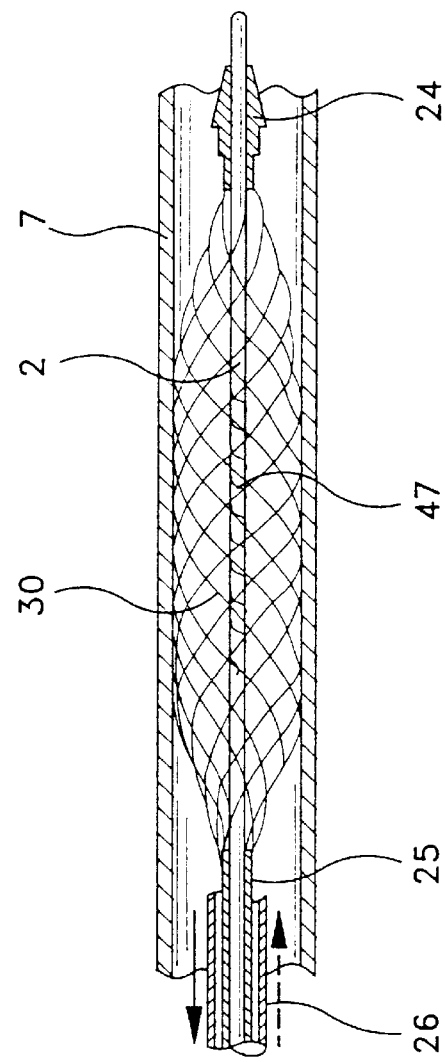
FIG. 6 is an axial cut of the sixth embodiment.

In the embodiment of FIG. 6 the catheter is formed of an end piece 24, a tubular conduit 25 at a distance from the end piece 24, a braided self expandable temporary stent 30 having one end affixed to the end piece 24 and the other end affixed to the tubular conduit 25, a tube 26 coaxial to and sliding over the tubular conduit 25 to enclose and free the self expandable stent 30. Inside the end piece 24 and the tubular conduit 25 is centered a guide wire 2 in sliding fit therein and a radioactive radiation emitter in the form of a filament 47 is coiled around the guide wire within the area occupied by the stent 30. For introduction into a blood vessel or coronary artery, the tube 26 is pushed over the stent 30 up to the end piece 24 thereby achieving collapse of the stent 30 over the guide wire 2. Once the stent is in the selected location in the vessel, the tube 26 is pulled back towards the proximal end of the system, thereby freeing the stent 30 which comes at rest against the wall of the vessel 7. The catheter is thus centered in the blood vessel and the radiation of the radioactive filament is uniformly applied to the vessel wall while the timing of irradiation may be selected at will because of the continuing blood flow through the braiding of the stent.

In all the embodiments of FIGS. 4 to 6, the radioactive treatment can be performed at any stage of the development or treatment of a stenosis, that is to say before or after balloon angioplasty or atherectomy because of the low profile of the system allowing penetration and centering even in narrowed vessels.

In all the embodiments shown, the guide wire and radioactive emitter may be fixed to the catheter instead of being movable within the catheter. As a further development, the catheter may comprise a guide wire for conventional entry into the blood vessel and the radioactive radiation emitter may be a filament affixed to or coiled around a wire intended to replace the said guide wire.

The radioactive radiation emitter can be under any appropriate form as described. Filaments will be however preferred because they can be safely fixed to the positioning means without the risk of any part of the emitter getting lost or without the risk of a container becoming untight, being thus safer than seed or powder or other forms. In addition, a further advantage of the filament is dense concentration of dose in a small diameter.

The radioactive radiation emitter can be selected at will, preferably however among beta emitters with a relatively short half-life, optimal penetration characteristics in tissue, and with a high radiation activity per specific gravity of the emitter (Bq/mg/mm3).

More specifically, a preferred choice will be a filament of 90 Yttrium which has a half-life of 2.7 days, a middle energy 0.942 Mev and maximal energy of 2.28 Mev, which would allow appreciable irradiation within a short distance from the filament, whereby only the internal layers of the vessel wall will be heavily irradiated while the more external structures will receive a dose which decreases with the square of the distance. Because of its mechanical characteristics, the filament of 90 Yttrium can have a diameter equal to or less than 0.9 mm. Subject to a heat elaboration under vacuum to avoid rapid oxidation and the resulting risk of breaking, the filament of 90 Yttrium can even have a diameter equal or less than 0.2 mm.

As described, the filament may be coiled around a guide wire or otherwise affixed to the guide wire in order to be integrated therewith. Accordingly, the filament may be for example welded to the guide wire.

A preferred approach is to make use of a guide wire of titanium which, after activation in a powerful field of neutrons will have a decay time of 5.8', and will advantageously solve the problem of undesirable long living of isotopes induction in other guide wires while providing mechanical qualities equivalent to those of stainless steel. In this environment, the filament will be either straight and affixed to the guide wire or coiled around the wire.

Although the balloon of the embodiments of FIGS. 1 to 3 has been shown and described as being substantially cylindrical, coaxial to the catheter, and annularly affixed by its ends to the catheter, other known shapes and catheter fixing for the balloon are possible. Also, the balloon may not be coaxial to the catheter, in which case the catheter will provide for the necessary shifting of the radioactive radiation emitter to assure its essential centering inside the balloon.

What is claimed is:

1. A medical device comprising:
   (a) a flexible catheter having a proximal portion and a distal portion, the distal portion sized and configured for intraluminal placement in a coronary blood vessel;
   (b) a beta radiation emitting source comprising 90 Yttrium disposed within the catheter distal portion; and
   (c) a balloon surrounding at least part of the catheter distal portion and adapted to radially expand and essentially radially center the beta radiation emitting source in the coronary blood vessel.

2. The medical device of claim 1, wherein the beta radiation emitting source comprises a filament.

3. The medical device of claim 2, wherein the filament diameter is less than or equal to 0.9 mm.

4. The medical device of claim 3, wherein the filament diameter is less than 0.2 mm.

5. The medical device of claim 2, wherein the filament is axially moveable within the catheter.

6. The medical device of claim 5, wherein the filament is adapted for insertion into and withdrawal from the catheter.

7. The medical device of claim 2, further comprising a guide wire slidably disposed within the catheter, wherein the filament is affixed to the guidewire.

8. The medical device of claim 2, wherein the filament is affixed to a titanium wire.

9. The medical device of claim 1, wherein the beta radiation emitting source is essentially axially centered within the balloon.

10. The medical device of claim 1, wherein the balloon is substantially cylindrical upon expansion and annularly affixed to the catheter.

11. The medical device of claim 10, wherein the balloon is adapted to perform a percutaneous transluminal angioplasty procedure.

12. A medical device comprising:
    (a) a flexible catheter having a proximal portion and a distal portion, the distal portion sized and configured for intraluminal placement in a coronary blood vessel;
    (b) a radiation emitting source disposed within the catheter distal portion, the radiation emitting source comprising 90 Yttrium adapted to irradiate a blood vessel wall without substantially irradiating tissue beyond the blood vessel wall; and
    (c) a balloon surrounding at least part of the catheter distal portion and adapted to radially expand and essentially center the radiation emitting source in the coronary blood vessel.

13. The medical device of claim 12, wherein the radiation emitting source comprises a filament.

14. The medical device of claim 13, wherein the filament diameter is less than or equal to 0.9 mm.

15. The medical device of claim 14, wherein the filament diameter is less than 0.2 mm.

16. The medical device of claim 13, further comprising a guide wire slidably disposed within the catheter, wherein the filament is affixed to the guidewire.

17. The medical device of claim 13, wherein the filament is affixed to a titanium wire.

18. The medical device of claim 12, wherein the radiation emitting source is essentially axially centered within the balloon.

19. The medical device of claim 13, wherein the filament is axially moveable within the catheter.

20. The medical device of claim 19, wherein the filament is adapted for insertion into and withdrawal from the catheter.

21. The medical device of claim 12, wherein the balloon is substantially cylindrical upon expansion and annularly affixed to the catheter.

22. The medical device of claim 21, wherein the balloon is adapted to perform a percutaneous transluminal angioplasty procedure.

23. The medical device of claim 12, wherein the radiation emitting filament is essentially axially centered within the balloon.

24. A medical device comprising:
    (a) a flexible catheter having a proximal portion and a distal portion, the distal portion sized and configured for intraluminal placement in a coronary blood vessel;
    (b) a radiation emitting filament comprising 90 Yttrium disposed within the catheter distal portion and having a diameter less than 0.2 mm; and
    (c) a balloon surrounding at least part of the catheter distal portion, and adapted to radially expand and essentially radially center the radiation emitting filament in the coronary blood vessel.

25. The medical device of claim 24, wherein the filament is axially moveable within the catheter.

26. The medical device of claim 25, wherein the filament is adapted for insertion into and withdrawal from the catheter.

27. The medical device of claim 24, further comprising a guide wire slidably disposed within the catheter, wherein the filament is affixed to the guidewire.

28. The medical device of claim 24, wherein the filament is affixed to a titanium wire.

29. The medical device of claim 24, wherein the balloon is substantially cylindrical upon expansion and annularly affixed to the catheter.

30. The medical device of claim 29, wherein the balloon is adapted to perform a percutaneous transluminal angioplasty procedure.

31. A medical device comprising:
    (a) a flexible catheter having a proximal portion and a distal portion, the distal portion sized and configured for intraluminal placement in a coronary blood vessel;
    (b) 90 Yttrium disposed within the catheter distal portion; and
    (c) a balloon surrounding at least part of the catheter distal portion and adapted to radially expand and essentially radially center the 90 Yttrium in the coronary blood vessel.

32. The medical device of claim 31, where in the 90 Yttrium is comprised in a filament.

33. The medical device of claim 32, wherein the filament is axially moveable within the catheter.

34. The medical device of claim 33, wherein the filament is adapted for insertion into and withdrawal from the catheter.

35. The medical device of claim 32, wherein the filament diameter is less than or equal to 0.9 mm.

36. The medical device of claim 35, wherein the filament diameter is less than 0.2 mm.

37. The medical device of claim 32, further comprising a guide wire slidably disposed within the catheter, wherein the filament is affixed to the guidewire.

38. The medical device of claim 32, wherein the filament is affixed to a titanium wire.

39. The medical device of claim 31, wherein the 90 Yttrium is essentially axially centered within the balloon.

40. The medical device of claim 31, wherein the balloon is substantially cylindrical upon expansion and annularly affixed to the catheter.

41. The medical device of claim 40, wherein the balloon is adapted to perform a percutaneous transluminal angioplasty procedure.

42. A method of preventing restenosis in a blood vessel comprising:
(a) providing a medical device comprising a flexible catheter having a proximal portion and a distal portion, the distal portion sized and configured for intraluminal placement in a coronary blood vessel; a beta radiation emitting source comprising 90 Yttrium disposed within the catheter distal portion; and a balloon surrounding at least part of the catheter distal portion and adapted to radially expand and essentially radially center the beta radiation emitting source in the coronary blood vessel;
(b) disposing the catheter distal portion at a treatment site with the beta radiation emitting source essentially radially centered within a blood vessel; and
(c) irradiating the treatment site with radiation including beta radiation and devoid of gamma radiation.

43. A method of preventing restenosis in a blood vessel comprising:
(a) providing a medical device comprising a flexible catheter having a proximal portion and a distal portion, the distal portion sized and configured for intraluminal placement in a coronary blood vessel; a radiation emitting source disposed within the catheter distal portion, the radiation emitting source comprising 90 Yttrium adapted to irradiate a blood vessel wall without substantially irradiating tissue beyond the blood vessel wall; and a balloon surrounding at least part of the catheter distal portion and adapted to radially expand and essentially center the radiation emitting source in the coronary blood vessel;
(b) disposing the catheter distal portion at a treatment site with the radiation emitting source essentially radially centered within a blood vessel formed of a blood vessel wall; and
(c) irradiating the blood wall without substantially irradiating tissue beyond the blood vessel wall.

44. A method of preventing restenosis in a blood vassal comprising:
(a) providing a medical device comprising a flexible catheter having a proximal portion and a distal portion, the distal portion sized and configured for intraluminal placement in a coronary blood vessel; a radiation emitting filament comprising 90 Yttrium disposed within the catheter distal portion and having a diameter less than 0.2 mm; and a balloon surrounding at least part of the catheter distal portion, and adapted to radially expand and essentially radially center the radiation emitting filament in the coronary blood vessel;
(b) disposing the catheter distal portion at a treatment site with the radiation emitting filament essentially radially centered within a blood vessel; and
(c) irradiating the treatment site.

45. A method of preventing restenosis in a blood vessel comprising:
(a) providing a medical device comprising a flexible catheter having a proximal portion and a distal portion, the distal portion sized and configured for intraluminal placement in a coronary blood vessel; 90 Yttrium disposed within the catheter distal portion; and a balloon surrounding at least part of the catheter distal portion and adapted to radially expand and essentially radially center the 90 Yttrium in the coronary blood vessel;
(b) disposing the catheter distal portion at a treatment site with the 90 Yttrium essentially radially centered within a blood vessel; and
(c) irradiating the treatment site.

* * * * *